United States Patent
Wang et al.

(10) Patent No.: US 10,127,661 B2
(45) Date of Patent: Nov. 13, 2018

(54) METHOD FOR EVALUATING SKIN TISSUE AND SYSTEM USING THE SAME

(71) Applicant: INDUSTRIAL TECHNOLOGY RESEARCH INSTITUTE, Hsinchu (TW)

(72) Inventors: Yen-Chang Wang, Taoyuan (TW); Chih-Ming Cheng, Fuxing Township (TW); Chir-Weei Chang, Taoyuan (TW); Chi-Shen Chang, Zhubei (TW); Sheng-Li Chang, Zhubei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 98 days.

(21) Appl. No.: 15/395,258

(22) Filed: Dec. 30, 2016

(65) Prior Publication Data

US 2017/0193659 A1   Jul. 6, 2017

Related U.S. Application Data

(60) Provisional application No. 62/275,191, filed on Jan. 5, 2016.

(30) Foreign Application Priority Data

Nov. 25, 2016  (TW) .............................. 105138870 A

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0066* (2013.01); *A61B 5/441* (2013.01);
(Continued)

(58) Field of Classification Search
CPC combination set(s) only.
See application file for complete search history.

(56) References Cited

U.S. PATENT DOCUMENTS

| 6,690,816 | B2 * | 2/2004 | Aylward | ............... G06T 7/0012 |
| | | | | 382/128 |
| 7,072,515 | B2 | 7/2006 | Al-Kofahi et al. | |

(Continued)

FOREIGN PATENT DOCUMENTS

| CN | 1662931 A | 8/2005 |
| CN | 101652784 A | 2/2010 |

(Continued)

OTHER PUBLICATIONS

Alex et al., "Multispectral in vivo Three-Dimensional Optical Coherence Tomography of Human Skin," Journal of Biomedical Optics, vol. 15, No. 2, Mar./Apr. 2010 (published online May 4, 2010), pp. 026025-1 to 026025-15.

(Continued)

*Primary Examiner* — Tsung-Yin Tsai
(74) *Attorney, Agent, or Firm* — Birch, Stewart, Kolasch & Birch, LLP

(57) ABSTRACT

A method for evaluating skin tissue includes: obtaining a tomographic image of skin; performing a quantization process for quantizing brightness values of the tomographic image of skin to generate a quantized image; performing a binarization process on the brightness value of each image point in the quantized image according to a first threshold interval to generate a first filtered image; performing the binarization process on the brightness value of each image point in the quantized image according to a second threshold interval to generate a second filtered image; obtaining a first estimated tissue boundary according to the distribution of the bright spots in the first filtered image; obtaining a second estimated tissue boundary according to the distribution of (Continued)

the bright spots in the second filtered image; estimating a thickness of skin tissue according to a difference between the first and second estimated tissue boundaries.

21 Claims, 14 Drawing Sheets

(51) Int. Cl.
*A61B 8/08* (2006.01)
*G06T 7/12* (2017.01)

(52) U.S. Cl.
CPC .............. *A61B 8/0858* (2013.01); *G06T 7/12* (2017.01); *A61B 2576/02* (2013.01); *G06T 2207/10101* (2013.01); *G06T 2207/30088* (2013.01)

(56) References Cited

U.S. PATENT DOCUMENTS

| | | | |
|---|---|---|---|
| 7,460,248 B2 | 12/2008 | Kurtz et al. | |
| 7,783,091 B2 | 8/2010 | Rinck et al. | |
| 2012/0035476 A1* | 2/2012 | Barthe | A61B 8/0858 600/439 |
| 2015/0099947 A1 | 4/2015 | Qu et al. | |
| 2015/0261998 A1* | 9/2015 | Yamanashi | G06T 5/003 382/103 |

FOREIGN PATENT DOCUMENTS

| | | |
|---|---|---|
| TW | I259765 B | 8/2006 |
| TW | I342201 B | 5/2011 |
| TW | I415029 B | 11/2013 |
| TW | I471117 B | 2/2015 |

OTHER PUBLICATIONS

Babalola et al., "Optical Coherence Tomography (OCT) of Collagen in Normal Skin and Skin Fibrosis," Arch Dermatol Res, Published online Oct. 10, 2013, 9 pages.

DiCanio et al., "Calculation of Apparent Age by Linear Combination of Facial Skin Parameters: A Predictive Tool to Evaluate the Efficacy of Cosmetic Treatments and to Assess the Predisposition to Accelerated Aging," Biogerontology, vol. 10, 2009 (Published online: Mar. 31, 2009), pp. 757-772.

Guinot et al., "Relative Contribution of Intrinsic vs Extrinsic Factors to Skin Aging as Determined by a Validated Skin Age Score," Arch Dermatol., vol. 138, Nov. 2002, pp. 1454-1460.

Lu et al., "Automated Analysis and Diagnosis of Skin Melanoma on Whole Slide Histopathological Images," Pattern Recognition, vol. 48, 2015 (Available online Mar. 5, 2015), pp. 2738-2750.

Nkengne et al. "The Skin Aging Index: A New Approach for Documenting Anti-aging Products or Procedures," Skin Research and Technology, vol. 19, 2013, pp. 291-298.

Trojahn et al., "Characterizing Facial Skin Ageing in Humans: Disentangling Extrinsic from Intrinsic Biological Phenomena," BioMed Research International, vol. 2015, Article ID 318586, 2015, pp. 1-9 (Total 10 pages).

Trojahn et al., "Measuring Skin Aging Using Optical Coherence Tomography in vivo: A Validation Study," Journal of Biomedical Optics, vol. 20, No. 4, Apr. 2015 (Published online Apr. 15, 2015), pp. 045003-1 to 045003-7 (Total 8 pages).

Trojahn et al., "Reliability and Validity of Two in vivo Measurements for Skin Surface Topography in Aged Adults," Skin Research and Technology, vol. 21, 2015, pp. 54-60.

Vierkötter et al., "The SCINEXA: A Novel, Validated Score to Simultaneously Assess and Differentiate between Intrinsic and Extrinsic Skin Ageing," Journal of Dermatological Science, vol. 53, 2009, pp. 207-211.

Xu et al., "Epidermis Segmentation in Skin Histopathological Images Based on Thickness Measurement and k-means Algorithm," EURASIP Journal on Image and Video Processing, vol. 2015, No. 18, 2015 (Published online Jun. 23, 2015), p. 1-14.

Yaar, "Clinical and Histological Features of Intrinsic Versus Extrinsic Skin Aging," Skin Aging (Chapter 2), Springer Berlin Heidelberg, 2006, pp. 9-21 (Total 14 pages).

Zedayko et al., "Caucasian Facial L* Shifts May Communicate Anti-ageing Efficacy," International Journal of Cosmetic Science, vol. 33, 2011, pp. 450-454.

Taiwanese Notice of Allowance and Search Report issued in Taiwanese Application No. 105138870 dated Mar. 7, 2017.

* cited by examiner

METHOD FOR EVALUATING SKIN TISSUE AND SYSTEM USING THE SAME

This application claims the benefit of a prior-filed provisional application Ser. No. 62/275,191, filed Jan. 5, 2016, and the benefit of Taiwan application Serial No. 105138870, filed Nov. 25, 2016, the subject matters of which are incorporated herein by references.

TECHNICAL FIELD

The disclosure relates in general to a method for evaluating skin tissue and system using the same.

BACKGROUND

To meet the enormous market demand in the fields of dermatology and medical cosmetology, when evaluating the conditions of a testee's skin, sometimes the tomography imaging technique (such as the optical coherence tomography (OCT) imaging technique) is used to generate a tomographic image of the testee's skin, which is further used as a basis for determining the conditions of the testee's skin.

However, for the tissue information contained in a known tomographic image of skin to be understood, the tomographic image of skin needs to be sighted and interpreted by doctors or other professional persons using their experience and expertise. However, this is very inconvenient for ordinary people who have a demand for skin detection but do not have the required medical background.

Therefore, how to provide a simple and effective method for evaluating skin tissue and a device using the same has become a prominent task for people in related technology fields.

SUMMARY

The disclosure is directed to a method for evaluating skin tissue and a system using the same capable of evaluating relevant parameters of a testee's skin tissue according to the result of imaging process of a tomographic image of the testee's skin.

According to one embodiment, a method for evaluating skin tissue is provided. The method includes: obtaining a tomographic image of skin; performing a quantization process for quantizing brightness values of the tomographic image of skin into a plurality of brightness levels to generate a quantized image; performing a binarization process on the brightness value of each image point in the quantized image according to a first threshold interval to generate a first filtered image, wherein in the quantized image, the image points whose brightness values fall within the first brightness threshold interval are set as bright spots in the first filtered image, and the image points whose brightness values fall outside the first brightness threshold interval are set as dark spots in the first filtered image; performing the binarization process on the brightness value of each image point in the quantized image according to a second threshold interval to generate a second filtered image, wherein in the quantized image, the image points whose brightness values fall within the second brightness threshold interval are set as bright spots in the second filtered image, and the image points whose brightness values fall outside the second brightness threshold interval are set as dark spots in the second filtered image; obtaining a first estimated tissue boundary according to the distribution of the bright spots in the first filtered image; obtaining a second estimated tissue boundary according to the distribution of the bright spots in the second filtered image; estimating a thickness of skin tissue according to a difference between the first and second estimated tissue boundaries.

According to another embodiment, a method for evaluating skin tissue is provided. The method includes: obtaining a tomographic image of skin; performing a noise elimination process on the tomographic image of skin to generate a noise eliminated image; performing a binarization process on the brightness value of each image point in the noise eliminated image to generate a binarized image including a plurality of bright blocks formed of aggregated bright spots; filtering the plurality of brightness blocks whose area is smaller than an area threshold off the binarized image to generate a reference image; detecting the bottom bright spots in all image columns of the reference image to obtain an outline of the bottom of the dermis, wherein each of the bottom bright spots in a corresponding image column of the reference image, unlike other bright spots in the corresponding image column, has a minimum height; detecting the top bright spots in all image columns of the reference image to obtain an outline of the top of the epidermis, wherein each of the top bright spots in a corresponding image column of the reference image, unlike other bright spots in the corresponding image column, has a maximum height; calculating an outline of the top of the dermis according to the outline of the top of the epidermis; and calculating at least one skin feature parameter according to the outline of the top of the epidermis, the outline of the bottom of the dermis and the outline of the top of the dermis.

The above and other aspects of the invention will become better understood with regard to the following detailed description of the preferred but non-limiting embodiment(s). The following description is made with reference to the accompanying drawings.

DETAILED DESCRIPTION

A number of embodiments of the present disclosure are disclosed below with reference to accompanying drawings. However, not every embodiment is illustrated in accompanying drawings. In practical applications, the present disclosure can have different variations and is not limited to the embodiments exemplified in the specification. A number of embodiments are disclosed in the present disclosure to meet the statutory requirements. Designations common to the accompanying drawings are used to indicate identical or similar elements.

Figure 1:
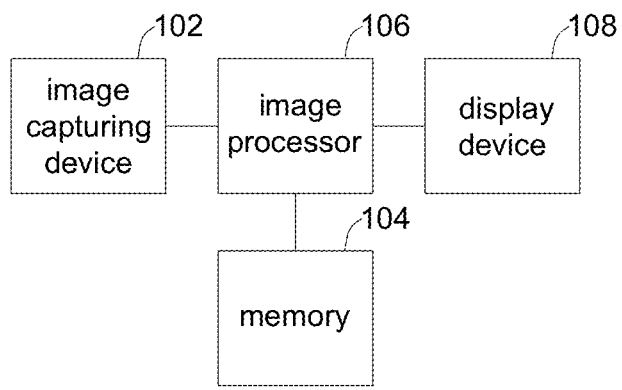
FIG. 1 is a block diagram of a skin tissue estimating system according to an embodiment of the disclosure.

FIG. 1 is a block diagram of a skin tissue estimating system 100 according to an embodiment of the disclosure. The skin tissue estimating system 100 mainly includes an image capturing device 102, a memory 104 and an image processor 106, and may selectively include a display device 108.

The image capturing device 102 may scan the testee's skin to obtain an input image. The image capturing device 102 can be realized by such as an optical coherence tomography (OCT) device, an ultrasonic scanning device, or other image device capable of obtaining a biological tissue through non-invasive scanning.

The memory 104 may store a programming code for the image processor 106 to perform the method for evaluating skin tissue according to an embodiment of the disclosure. The memory 104 can be realized by any types of non-volatile memory.

The image processor 106 couples the image capturing device 102 and the memory 104, and performs the method for evaluating skin tissue in an embodiment of the disclosure on the input image captured by the image capturing device 102 to generate corresponding parameters of skin features. The image processor 106 can be realized by a central processing unit, a micro-processor or other electronic circuits equipped with an image processing function.

In an embodiment, the skin tissue estimating system 100 further includes a display device 108. The display device 108 can be realized by a display located at a display connected to the image processor 106 at a local end and or realized by a display monitor of a device at a remote end. The display device 108 may provide a human-machine interface, such as a patterned user interface, to visually display relevant information of the testee's skin, such as the parameters of skin features.

Figure 2:
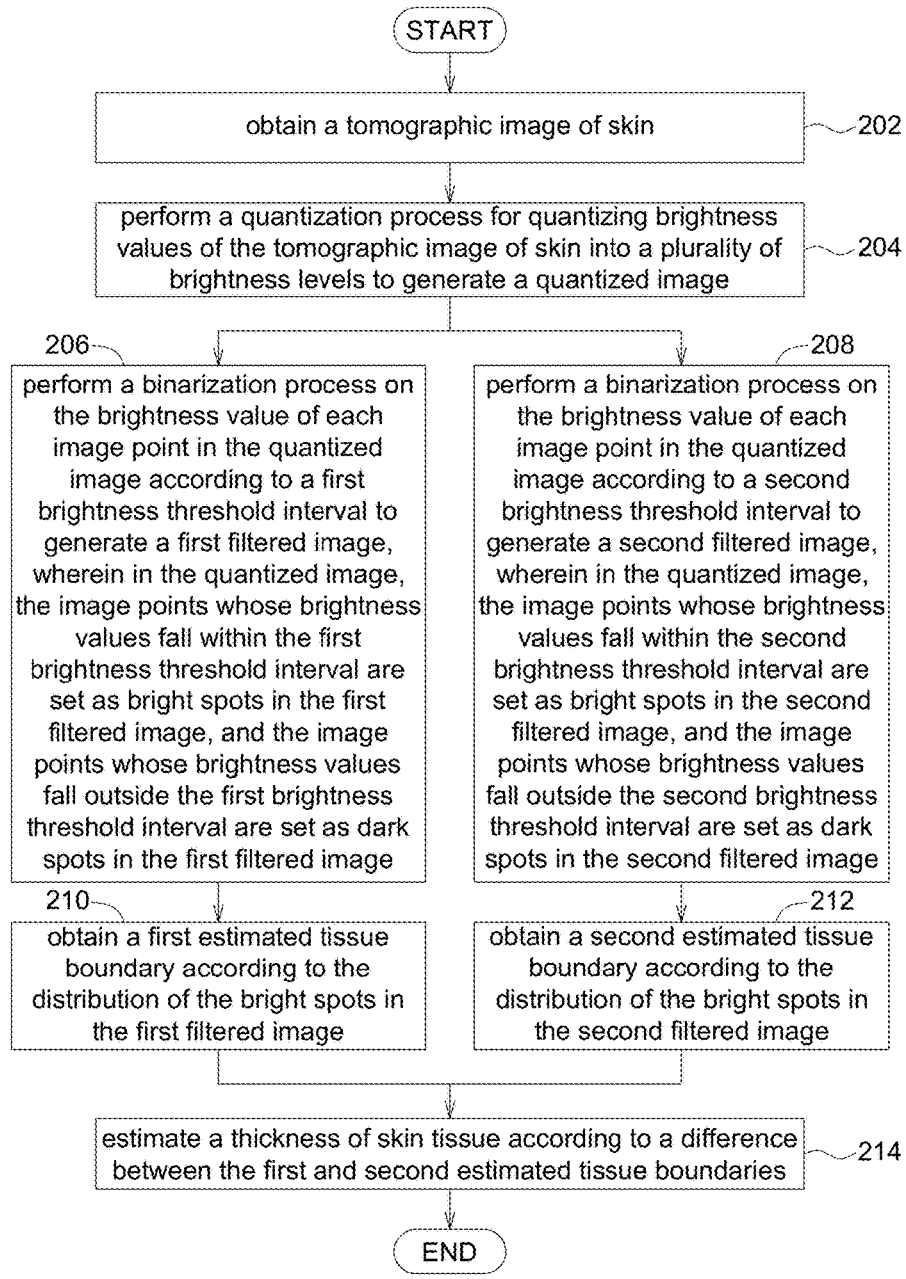
FIG. 2 is a flowchart of a method for evaluating skin tissue according to an embodiment of the disclosure.

FIG. 2 is a flowchart of a method for evaluating skin tissue according to an embodiment of the disclosure. The method for evaluating skin tissue can be performed by the image processor 106 of the skin tissue estimating system 100.

In step 202, a tomographic image of skin is obtained by the image processor 106. The tomographic image of skin, such as the input image obtained by scanning the testee's skin using the image capturing device 102 (such as an OCT image of skin or a ultrasonic image of skin), depends on the types of the image capturing device 102.

In an embodiment, the user may define a target processing range in the input image and may further use a part of the target processing range as a tomographic image of skin.

In an embodiment, the image processor 106 firstly performs an intensity normalization process on the input image and then uses the intensity normalized input image as a tomographic image of skin.

The intensity normalization process includes: detecting an average brightness value of the part of the input image corresponding to the epidermal reflective area (such as the area AA of FIG. 4A) by the image processor 106, and sequentially shifting the overall brightness value of the input image such that the average brightness value can be adjusted to a default value. Let the range of brightness values be set as 0~255. Exemplarily but not restrictively, the default value can be set as 230.

Since the part of the input image corresponding to the epidermal reflective area is normally the brightest part in the image, by defining the brightness value of a part of the input image, the overall brightness of the input image can be adjusted to a suitable range, such that the features of skin tissue can be obtained through image analysis according to a default brightness threshold.

In step 204, a quantization process is performed for quantizing brightness values of the tomographic image of skin into a plurality of brightness levels by the image processor 106 to generate a quantized image. For example, suppose original brightness values of the tomographic image of skin range between 0~255. After the original brightness values are quantized into k brightness levels, the range of brightness values being 0~255 will be divided into k equal intervals, wherein the image points whose brightness values fall within the same interval will be categorized as the same brightness level and have the same brightness value. Thus, the quantized image will have only k possible brightness values. In an embodiment, the image processor 106 may quantize the brightness values of the tomographic image of skin into k brightness levels using the Kmeans algorithm to generate a quantized image.

In step 206, a binarization process is performed on the brightness value of each image point in the quantized image by the image processor 106 according to a first threshold interval to generate a first filtered image, wherein in the quantized image, the image points whose brightness values fall within the first brightness threshold interval are set as bright spots in the first filtered image, and the image points whose brightness values fall outside the first brightness threshold interval are set as dark spots in the first filtered image.

For example, if the quantized image has 8 brightness levels (that is, k=8) and the first brightness threshold interval covers the $5^{th}$ to the $7^{th}$ brightness levels, then in the quantized image, the image points whose brightness values fall on the $5^{th}$ to the $7^{th}$ brightness levels are set as bright spots, and the image points whose brightness values fall on the $1^{st}$, $2^{nd}$, $3^{rd}$, $4^{th}$, $8^{th}$ brightness levels are set as dark spots to form the first filtered image.

According to the binarization mechanism, the brightness value of the bright spot is set as the maximum brightness value (such as 255), and the brightness value of the dark spot is set as the minimum brightness value (such as 0).

In step 208, a binarization process is performed on the brightness value of each image point in the quantized image by the image processor 106 according to a second threshold interval to generate a second filtered image, wherein in the quantized image, the image points whose brightness values fall within the second brightness threshold interval are set as bright spots in the second filtered image, and the image points whose brightness values fall outside the second brightness threshold interval are set as dark spots in the second filtered image.

The second brightness threshold interval can be different from the first brightness threshold interval. For example, if the quantized image has 8 brightness levels, and the second brightness threshold interval covers the $2^{nd}$ to the $8^{th}$ brightness levels, then in the quantized image, the image points whose brightness values fall on the $2^{nd}$ to the $8^{th}$ brightness levels are set as bright spots, and the image points whose brightness values fall on the $1^{st}$ brightness level are set as dark spots to form the second filtered image.

Similarly, according to the binarization mechanism, the brightness value of the bright spot is set as the maximum brightness value (such as 255), and the brightness value of the dark spot is set as the minimum brightness value (such as 0).

Since the tissue of each layer of the skin (such as the epidermis or the dermis) has light and shade changes in a gray level image, the distribution of the bright spots in the first and second filtered images generated by performing a binarization process on the image points falling within the first and the second brightness threshold interval will carry feature information of skin tissue.

In steps 210 and 212, a first estimated tissue boundary and a second estimated tissue boundary are obtained by the image processor 106 according to the distribution of the bright spots in the first filtered image and the second filtered image, respectively.

The first and second estimated tissue boundaries can be an estimated top position of the dermis, an estimated bottom position of the dermis, or an estimated top position of the epidermis.

In step 214, a thickness of skin tissue is estimated by the image processor 106 according to a difference between the first and second estimated tissue boundaries. For example, if the first and second estimated tissue boundaries respectively denote the estimated top position of the dermis and the estimated bottom position of the dermis, then the difference between the first and second estimated tissue boundaries denotes the dermal thickness.

It should be noted that although in the embodiment of FIG. 2, the first and second estimated tissue boundaries are obtained by processing the quantized image according to the first and second brightness threshold intervals respectively. However, the disclosure is not limited thereto. In an embodiment, the image processor 106 may further process the quantized image according to a third brightness threshold interval to obtain a third estimated tissue boundary. The third estimated tissue boundary can be an estimated top position of the dermis, an estimated bottom position of the dermis, or an estimated top position of the epidermis.

Furthermore, the image processor 106 may perform a binarization process on the brightness value of each image point in the quantized image according to the third brightness threshold interval to generate a third filtered image, wherein in the quantized image, the image points whose brightness values fall within the third brightness threshold interval are set as bright spots in the third filtered image, and in the quantized image, the image points whose brightness values fall outside the third brightness threshold interval are set as dark spots in the third filtered image. Then, the image processor 106 obtains the third estimated tissue boundary according to the distribution of the bright spots in the third filtered image, and estimates another thickness of skin tissue according to a difference between the third estimated tissue boundary and the first estimated tissue boundary or a difference between the third estimated tissue boundary and the second estimated tissue boundary. For example, if the first estimated tissue boundary and the third estimated tissue boundary respectively denote an estimated top position of the dermis and an estimated top position of the epidermis, then the difference between the two positions denotes an epidermal thickness.

An exemplary method for evaluating skin tissue is described below with FIGS. 3~12 so that the disclosure can be more clearly understood.

Figure 3:
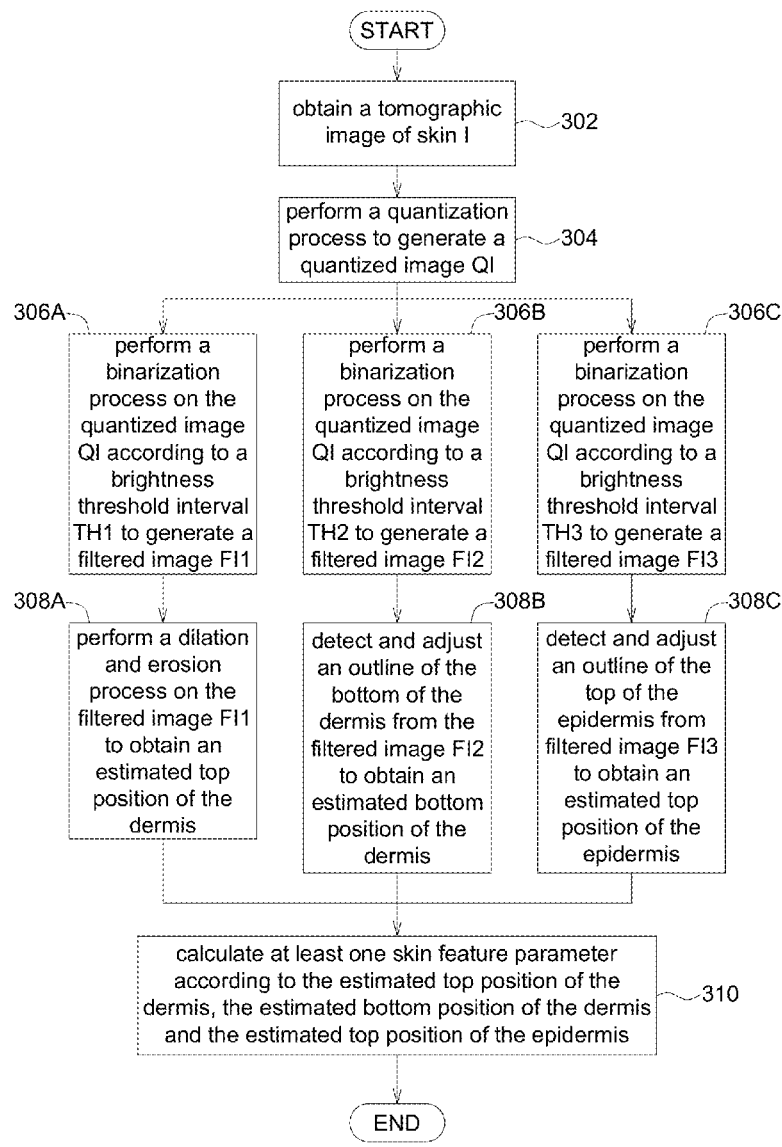
FIG. 3 is a flowchart of a method for evaluating skin tissue according to an embodiment of the disclosure.

FIG. 3 is a flowchart of a method for evaluating skin tissue according to an embodiment of the disclosure. The method for evaluating skin tissue can be performed by the image processor 106 of the skin tissue estimating system 100.

Figure 4A:
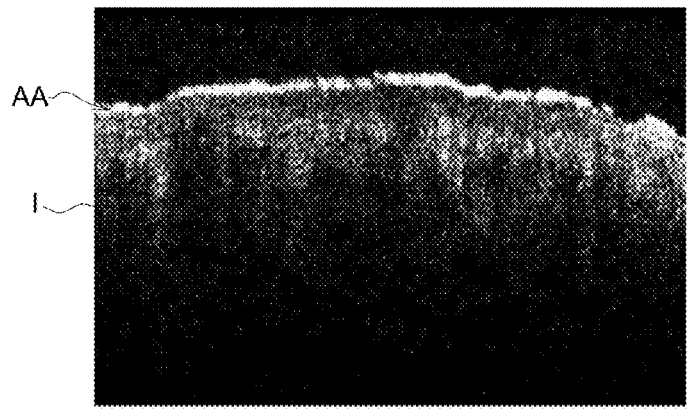
FIG. 4A is an exemplary tomographic image of skin.

In step 302, a tomographic image of skin I is obtained by the image processor 106. The tomographic image of skin I can be an intensity normalized skin OCT gray level image as indicated in FIG. 4A.

Figure 4B:
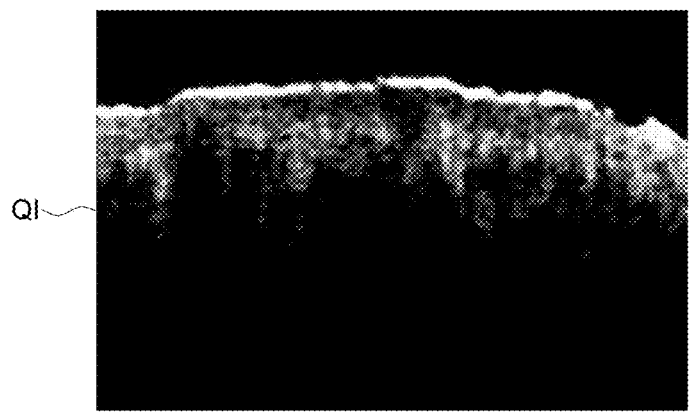
FIG. 4B is an exemplary quantized image.

In step 304, a quantization process is performed on the tomographic image of skin I by the image processor 106 (such as using the Kmeans algorithm) for quantizing brightness values of the tomographic image of skin I into k brightness levels to generate a quantized image QI, wherein the brightness values, ranked in an ascending order, are $1^{st}$ brightness level, $2^{nd}$ brightness level, $3^{rd}$ brightness level, . . . , and $k^{th}$ brightness level. As indicated in FIG. 4B, the tomographic image of skin I is quantized as the quantized image QI having 8 brightness levels.

After the quantized image QI is obtained, the image processor 106 may obtain feature information of the top of the dermis through steps 306A and 308A, obtain feature information of the bottom of the dermis through steps 306B and 308B, and obtain feature information of the top of the epidermis through steps 306C and 308C.

It should be noted although the above steps are illustrated side by side, such illustration is not for limiting the sequence of the steps. Based on actual needs in practical applications, the image processor 106 may perform the steps concurrently or sequentially, or the image processor 106 may perform some steps concurrently but some other steps sequentially.

Figure 5:
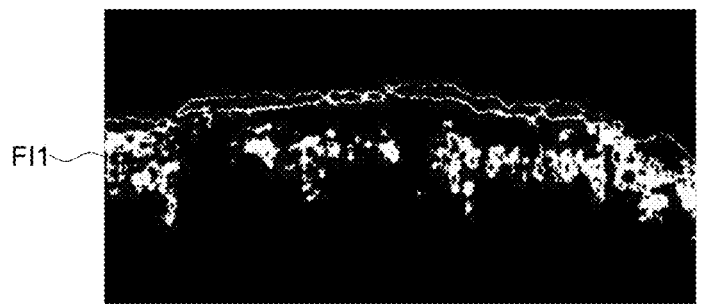
FIG. 5 is an exemplary filtered image.

In step 306A, a binarization process is performed on the quantized image QI by the image processor 106 according to a brightness threshold interval TH1 (the first brightness threshold interval) to generate a filtered image FI1. As indicated in FIG. 5, a filtered image FI1 is obtained by performing a binarization process on the quantized image QI if the brightness threshold interval TH1 covers the $5^{th}$ to the $7^{th}$ brightness levels. In the quantized image QI, the image points whose brightness values fall on the $5^{th}$ to the $7^{th}$ brightness levels are set as bright spots, and the image points whose brightness values fall on the $1^{st}$, the $2^{nd}$, the $3^{rd}$, the $4^{th}$, and the $8^{th}$ brightness levels are set as dark spots.

In the present example, the brightness threshold interval TH1 is set as the $5^{th}$ to the $7^{th}$ brightness levels. This is because the study shows that the dermal tissue normally corresponds to brighter part (that is, the image points having larger brightness levels) in the image. Since the top of the epidermis is normally the brightest part in the image due to the reflection of the light on the interface, in the present embodiment, the image points having the largest brightness level (the $8^{th}$ brightness level) are excluded from the brightness threshold interval TH1 to avoid the brightness information of the top of the epidermis interfering with the analysis of the features of dermal tissue.

Figure 6:
FIG. 6 is an exemplary repaired image.

In step 308A, a dilation and erosion process is performed on the filtered image FI1 by the image processor 106 to generate a repaired image FI1', and an estimated top position of the dermis (the first estimated tissue boundary) is obtained according to the repaired image FI1'. As indicated in FIG. 6, an exemplary repaired image FI1' is obtained by performing a dilation and erosion process on the filtered image FI1.

According to the algorithm mechanism of the dilation and erosion process, the repaired image FI1' includes a plurality of bright blocks formed of aggregated bright spots. The image processor 106 may calculate an estimated position of the dermal top according to an average height of the bright blocks at the top of the repaired image FI1'.

Furthermore, since the distribution of the bright blocks in the repaired image FI1' basically depicts the distribution of the dermal tissue, the top position of the dermis can be estimated according to the average height of the bright blocks at the top of the repaired image FI1'.

Details of calculating the estimated top position of the dermis according to the distribution of the bright blocks in the repaired image FI1' are illustratively disclosed below with the non-limiting embodiment of FIG. 7.

Figure 7:
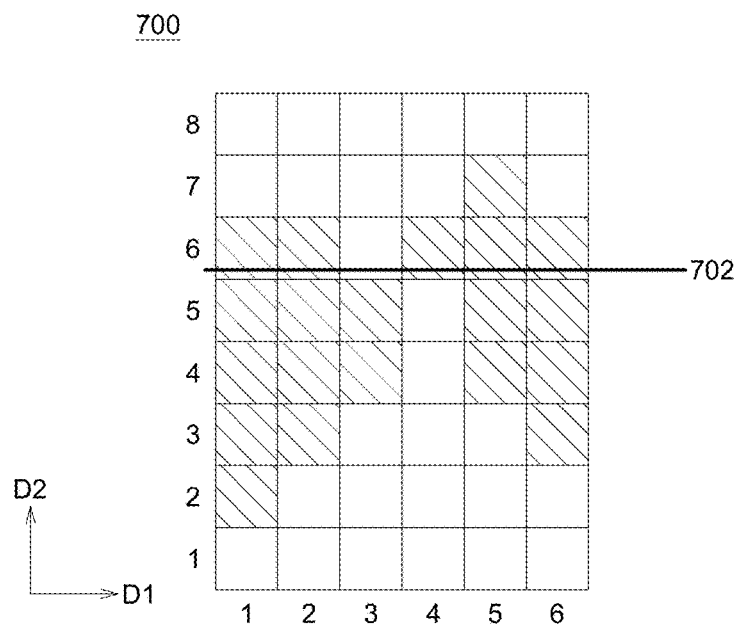
FIG. 7 is a schematic diagram of a partial image of a repaired image.

FIG. 7 is a schematic diagram of a partial image 700 of a repaired image FI1'. The partial image 700 includes many image points, and each image point is represented by a grid, wherein the grid with slash shading denotes the bright spot, and the grid without slash shading denotes the dark spot.

In the example of FIG. 7, the partial image 700 includes 6 image columns defined along a first direction D1 and 8 image rows defined along a second direction D2.

To maintain consistency in the description of the algorithm disclosed in an embodiment of the disclosure, when the lower part of an image corresponds to the skin tissue (as indicated in FIG. 4A, the lower part of the image corresponds to the skin tissue and the upper part corresponds to the air), the horizontal direction of the image is defined as the first direction D1, and the vertical direction of the image is defined as the second direction D2. Therefore, in the present specification, the position expressions such as "above" and "under" are defined according to the second direction D2.

Moreover, in the present embodiment, the height of an image point is defined as the row position of the image point in an image column along the second direction D2. For example, the height of the image point (1,4) located at the $1^{st}$ image column and the $4^{th}$ row of the partial image 700 is 4, and the height of the image point (2,7) located at the $2^{nd}$ image column and the $7^{th}$ row of the image point is 7, and the rest can be obtained by the same analogy.

It should be noted that in the present embodiment, the definition of height is for conveniently indicating the image point at a particular position, not for limiting the parameters used in the algorithm. In some embodiments, the image point at the same position can be represented using other coordinate systems. For example, when the coordinate of each image point is defined using the X-Y coordinate system (the X axis is defined as the first direction D1, and the Y axis is defined as the inverse direction of the second direction D2) whose original point is at the top left corner of the partial image 700. Meanwhile, the coordinate of the image point being (1,1) in the original D1-D2 coordinate system changes to (1,8) in the X-Y coordinate system, and the coordinate of the image point being (2,3) in the original D1-D2 coordinate system changes to (2,6) in the X-Y coordinate system, and the rest can be obtained by the same analogy.

In the present embodiment, the image processor 106 may calculate an estimated top position of the dermis (DermToA) according to the following formula:

$$DermToA = \frac{1}{N}\sum_i n_i H_i$$

Wherein, N denotes the total number of bright spots in the image; $n_i$ denotes the quantity of bright spots in the $i^{th}$ image column; $H_i$ denotes the height of the topmost bright spot in the $i^{th}$ image column.

Let FIG. 7 be taken for example. The partial image 700 includes 20 bright spots, wherein the $1^{st}$ image column has 5 bright spots, the $2^{nd}$ image column has 4 bright spots, the $3^{rd}$ image column has 2 bright spots, the $4^{th}$ image column has 1 bright spot, the $5^{th}$ image column has 4 bright spots, and the $6^{th}$ image column has 4 bright spots. Moreover, the coordinate of the topmost bright spot in the $1^{st}$ image column is (1,6), and the height is 6; the coordinate of the topmost bright spot in the $2^{nd}$ image column is (2,6), and the height is 6; the coordinate of the topmost bright spot in the $3^{rd}$ image column is (3,5), and the height is 5; the coordinate of the topmost bright spot in the $4^{th}$ image column is (4,6), and the height is 6; the coordinate of the topmost bright spot in the $5^{th}$ image column is (5,7), and the height is 7; the coordinate of the topmost bright spot in the $6^{th}$ image column is (6,6), and the height is 6.

The image processor 106 may detect and count the bright spots in the image to obtain the above information, and may further calculate an estimated top position of the dermis according to the following formula:

DermToA=5/20×6+4/20×6+2/20×5+1/20×6+4/20×7+ 4/20×6=6.1

In the example of FIG. 7, the top boundary of the dermis approximately has a height of 6.1 in the image. The horizontal line 702 whose height is 6.1 indicates the estimated position of the top of the dermis.

Figure 8:
FIG. 8 is an exemplary filtered image.

Refer to FIG. 3. In step 306B, a binarization process is performed on the quantized image by the image processor 106 according to a brightness threshold interval TH2 (such as the second brightness threshold interval) to generate a filtered image FI2. As indicated in FIG. 8, a filtered image FI2 obtained by performing a binarization process on the quantized image QI if the brightness threshold interval TH2 covers the $2^{nd}$ to the $8^{th}$ brightness levels. In the quantized image QI, the image points whose brightness values fall on the $2^{nd}$ to the $8^{th}$ brightness levels are set as bright spots in the filtered image FI2, and the image points whose brightness values fall on the $1^{st}$ brightness level are set as dark spots in the filtered image FI2.

In the present example, the brightness threshold interval TH2 is set as the $2^{nd}$ to the $8^{th}$ brightness levels to exclude the noises having low brightness values from the image.

In step 308B, an outline of the bottom of the dermis is detected from the filtered image FI2 and adjusted by the image processor 106 to obtain an estimated bottom position of the dermis (such as the second estimated tissue boundary). The outline of the bottom of the dermis is formed by linking the bottom bright spots in all image columns of the filtered image FI2. Each of the bottom bright spots in a corresponding image column of the filtered image FI2, unlike other bright spots in the corresponding image column, has a minimum height.

The image processor 106 may detect the heights of a plurality of bottom bright spots in the filtered image FI2, and then calculate an estimated bottom position of the dermis according to the heights of the bottom bright spots. For example, after detecting and adjusting the outline of the bottom of the dermis, the image processor 106 may calculate an estimated bottom position of the dermis according to the height information of the bottom bright spots in the outline of the bottom of the dermis, wherein the height information is such as the average height, the maximum height, or the minimum height. For example, the image processor 106 generates the estimated bottom position of the dermis based on the height information of the bottom bright spots in the outline of the bottom of the dermis according to the weighting average of the average height, the maximum height and the minimum height of the bottom bright spots.

In an embodiment, the image processor 106 may calculate an estimated bottom position of the dermis (DermBoA) according to the following formula:

$$DermBoA = w_1 * (\text{average height}) + w_2 * (\text{maximum height}) + w_3 * (\text{minimum height})$$

Wherein $w_1$, $w_2$, $w_3$ are weighting factors. In an example, $w_1$ ranges between 0.4~0.6, $w_2$ ranges between 0.2~0.3, and $w_3$ ranges between 0.2~0.3. For example, $w_1=0.5$, $w_2=0.25$, $w_3=0.25$.

In an embodiment, the image processor 106 may adjust the outline of the bottom of the dermis according to one or more than one criterion of determination, such that the adjusted outline may reflect the bottom contour of the dermis more truthfully.

Since the height of the bottom of the dermis does not exceed the height of the top of the dermis, the image processor 106 may determine whether the height of a first bottom bright spot of the bottom bright spots is larger than the estimated top position of the dermis, and further adjusts the height of the first bottom bright spot to be smaller than the estimated top position of the dermis if the result of determination is affirmative. If the result of determination is negative, the image processor 106 may preserve the height of the first bottom bright spot, or may determine whether to adjust the height of the first bottom bright spot according to other criteria of determination.

For example, the image processor 106 may determine whether it is possible that the first bottom bright spot is an image noise according to whether a height difference between the first bottom bright spot and a second bottom bright spot of the bottom bright spots is larger than a height threshold. The first bottom bright spot and the second bottom bright spot are respectively located at two adjacent image columns in the filtered image FI2.

If the height difference between the first bottom bright spot and the second bottom bright spot in an adjacent image column (such as previous image column) is too large (over a height threshold), this indicates that the first bottom bright spot could be an un-filtered image noise. Meanwhile, the image processor 106 may further determine whether the quantity of bright spots in a default segment above the image column at which the first bottom bright spot is located is larger than a quantity threshold to assure that the quantity of bright spots above the first bottom bright spot is sufficient (for example, the bright spots occupy 50% of the default segment). If the result of determination is affirmative, this indicates that the first bottom bright spot belongs to the image of the dermal tissue, and the height of the first bottom bright spot will not be adjusted. Conversely, if the result of determination is negative, then the image processor 106 will treat the first bottom bright spot as an image noise, and adjust the height of the first bottom bright spot to the height of the second bottom bright spot.

Details of adjusting the outline of the bottom of the dermis detected from the filtered image FI2 are illustratively disclosed below with the non-limiting embodiment of FIG. 9.

Figure 9:
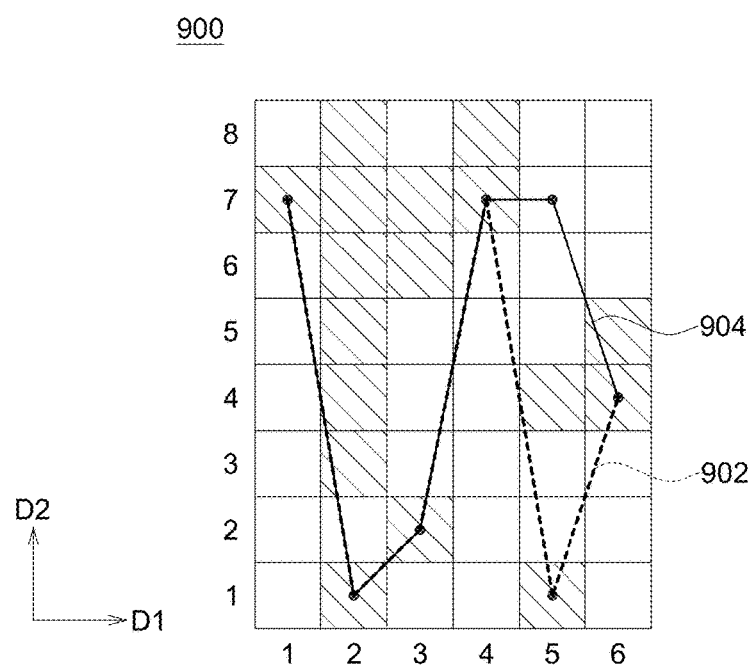
FIG. 9 is a schematic diagram of a partial image of a filtered image.

FIG. 9 is a schematic diagram of a partial image 900 of a filtered image FI2. The partial image 900 includes many image points, and each image point is represented by a grid, wherein the grid with slash shading denotes the bright spot, and the grid without slash shading denotes the dark spot.

Prior to adjustment, a bottom bright spot is bright spot whose height is the minimum in an image column. As indicated in FIG. 9, the bottom bright spots in all image columns are respectively located at coordinates (1,7), (2,1), (3,2), (4,7), (5,1), (6,4). The bottom bright spots in all image columns can be sequentially linked to form an un-adjusted outline of the bottom of the dermis as indicated in curve 902.

Curve 904 represents the outline of the bottom of the dermis having been adjusted according to the above mechanism. Let the height threshold=5 image points (pixel points). Although the height difference between the bottom bright spot (2,1) in the $2^{nd}$ image column and the bottom bright spot (1,7) in the $1^{st}$ image column is 6 being larger than the height threshold, the quantity of bright spots above the bottom bright spot in the $2^{nd}$ image column is sufficient, and therefore the height of the bottom bright spot (2,1) does not need to be adjusted.

Conversely, although the height difference between the bottom bright spot in the $4^{th}$ image column and the bottom bright spot in the $4^{th}$ image column is also 6, the bottom bright spot in the $4^{th}$ image column is replaced with the bright spot (5,7) having the same height with the bottom bright spot in the $4^{th}$ image column. Since there is only one bright spot above the bottom bright spot in the $4^{th}$ image column, the quantity of bright spots is insufficient. After adjustment, the bottom bright spots in all image columns are sequentially linked to form an adjusted outline of the bottom of the dermis as indicated in curve 904.

Figure 10:
FIG. 10 is an exemplary filtered image.

Return to FIG. 3. In step 306C, a binarization process is performed on the quantized image QI by the image processor 106 according to a brightness threshold interval TH3 (such as the third brightness threshold interval) to generate a filtered image FI3 (such as the third filtered image). As indicated in FIG. 10, if the brightness threshold interval TH3 covers the $4^{th}$ to the $8^{th}$ brightness levels, the image points whose brightness values fall on the $4^{th}$ to the $8^{th}$ brightness levels are set as bright spots in the filtered image FI3, and the image points whose brightness values fall on the $1^{st}$ to the $3^{rd}$ brightness levels are set as dark spots in the filtered image FI3.

In step 308C, an outline of the top of the epidermis is detected from filtered image FI3 and adjusted by the image processor 106 to obtain an estimated top position of the epidermis (such as the third estimated tissue boundary).

The outline of the top of the epidermis is formed by linking the top bright spots in all image columns of the filtered image FI3. Each of the top bright spots in a corresponding image column of the filtered image FI3, unlike other bright spots in the corresponding image column, has a maximum height.

The image processor 106 may detect the heights of a plurality of top bright spots in the filtered image FI3, and then calculate an estimated top position of the epidermis according to the heights of the top bright spots. For example, after detecting and adjusting the outline of the top of the epidermis, the image processor 106 may calculate an estimated top position of the epidermis according to the height information of the top bright spots in the outline of the top of the epidermis, wherein the height information is such as the average height, the maximum height, or the minimum height. For example, the image processor 106 generates the estimated top position of the epidermis based on the height information of the top bright spots in the outline of the top of the epidermis according to the weighting average of the average height, the maximum height and the minimum height of the top bright spots.

In an embodiment, the image processor 106 may calculate an estimated top position of the epidermis (EpidermToA) according to the following formula:

$$\text{EpidermToA} = w_1 *(\text{average height}) + w_2 *(\text{maximum height}) + w_3 *(\text{minimum height})$$

Wherein $w_1$, $w_2$, $w_3$ are weighting factors. The weighting factors $w_1$, $w_2$, $w_3$ used for calculating the estimated top position of the epidermis are, for example, the same as the weighting factors used for calculating the estimated bottom position of the dermis disclosed above.

In an embodiment, the image processor 106 may adjust the outline of the top of the epidermis according to one or more than one criterion of determination, such that the adjusted outline may reflect the top contour of the epidermis more truthfully.

For example, the image processor 106 may determine whether it is possible that the first top bright spot is an image noise according to whether a height difference between a first top bright spot of the top bright spots and a second top bright spot of the top bright spots is larger than a height threshold. The first top bright spot and the second top bright spot are respectively located at two adjacent image columns in the filtered image FI3.

If it is determined that the height difference between the first top bright spot and the second top bright spot is larger than the height threshold, the first top bright spot will be regarded as an image noise, Meanwhile, the image processor 106 adjusts the height of the first top bright spot, such that the height difference between the first top bright spot and the second top bright spot is smaller than the height threshold.

In an embodiment, if it is determined that the height difference between the first top bright spot and the second top bright spot is larger than the height threshold, the image processor 106 may determine whether there are any bright spots existing in a default interval (such as 5 image points) under the image column at which the first top bright spot is located. If the result of determination is affirmative, the first top bright spot is updated as the bright spot whose height is the maximum in the default interval. If the result of determination is negative, the height of the first top bright spot is adjusted to the height of the second top bright spot.

Details of adjusting the outline of the top of the epidermis detected from the filtered image FI3 are illustratively disclosed below with the non-limiting embodiment of FIG. 11.

Figure 11:
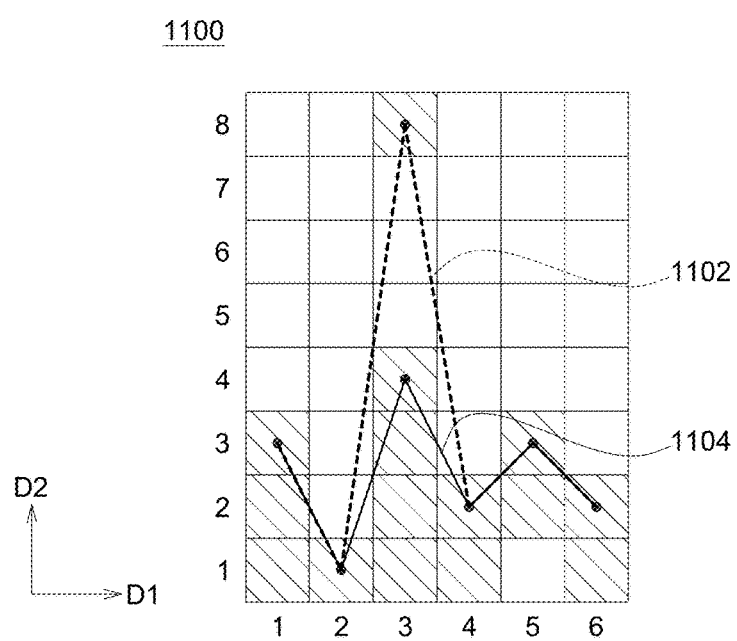
FIG. 11 is a schematic diagram of a partial image of a filtered image.

FIG. 11 is a schematic diagram of a partial image 1100 of a filtered image FI3. The partial image 1100 includes many image points, and each image point is represented by a grid, wherein the grid with slash shading denotes the bright spot, and the grid without slash shading denotes the dark spot.

A top bright spot is a bright spot whose height is the minimum in an image column. As indicated in FIG. 11, the top bright spots in all image columns are respectively located at coordinates (1,3), (2,1), (3,8), (4,2), (5,3), (6,2). The top bright spots in all image columns can be sequentially linked to form an un-adjusted outline of the top of the epidermis as indicated in curve 1102.

Curve 1104 represents the outline of the top of the epidermis having been adjusted according to the above mechanism. Let the height threshold=5 image points (pixel points). Since the height difference between the top bright spot (3,8) in the $3^{rd}$ image column and the top bright spot (2,1) in the $2^{nd}$ image column is 7 being larger than the height threshold, and the bright spots (3,3) and (3,4) exist in a default interval (5 image points) under the top bright spot in the $3^{rd}$ image column, the bright spot (3,4) whose height is the maximum in the default interval is used as a new top bright spot. After adjustment, the top bright spots in all image columns are sequentially linked to form an adjusted outline of the top of the epidermis as indicated in curve 1104.

Figure 12:
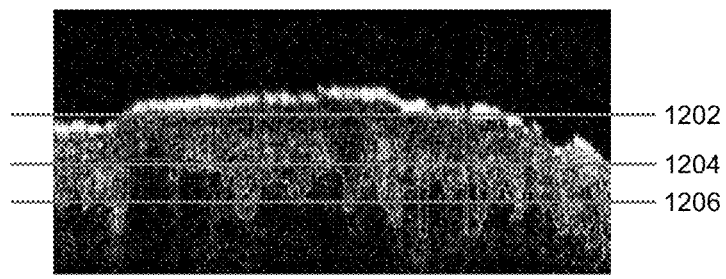
FIG. 12 is a relationship diagram of estimated tissue boundary vs tomographic image of skin.

FIG. 12 is a relationship diagram of estimated tissue boundary vs tomographic image of skin I. As indicated in FIG. 12, the heights of the horizontal lines 1202, 1204 and 1206 are the estimated top position of the epidermis, the estimated top position of the dermis and the estimated bottom position of the dermis, respectively. Although the epidermal tissue and the dermal tissue have irregular contours in the tomographic image of skin I, the thickness between the tissues still can be clearly seen through a variation in the heights of the horizontal lines 1202, 1204 and 1206.

Return to FIG. 3. In step 310, at least one skin feature parameter, such as the epidermal thickness or the dermal thickness, is calculated by the image processor 106 according to the estimated top position of the dermis, the estimated bottom position of the dermis and the estimated top position of the epidermis.

For example, the image processor 106 may calculate an epidermal thickness (EpidermTh) according to a difference between the estimated top position of the epidermis (EpidermToA) and the estimated top position of the dermis (DermToA):

$$\text{EpidermTh} = \text{EpidermToA} - \text{DermToA}$$

The image processor 106 may calculate the dermal thickness (DermTh) according to a difference between the estimated top position of the dermis (DermToA) and the estimated bottom position of the dermis (DermBoA):

$$\text{DermTh} = \text{DermToA} - \text{DermBoA}$$

Besides, after a dermal area is defined in the tomographic image of skin I according to the estimated top position of the dermis and the estimated bottom position of the dermis (or the outline of the bottom of the dermis) and the image points whose brightness is smaller than a threshold are filtered off the dermal area, the image processor 106 may calculate an average brightness value of the dermal area to obtain a collagen index positively correlated with the density of the dermal collagen.

As indicated in the flowchart of FIG. 3, after obtaining the quantized image of the tomographic image of skin, the image processor 106 may perform a binarization process on the quantized image according to different brightness intervals to obtain a corresponding filtered image, and then may calculate an estimated tissue boundary of each layer, such as an estimated top position of the dermis, an estimated bottom position of the dermis and an estimated top position of the epidermis, according to the filtered images. The obtained estimated tissue boundary is used for calculating at least one skin feature parameter.

Figure 13:
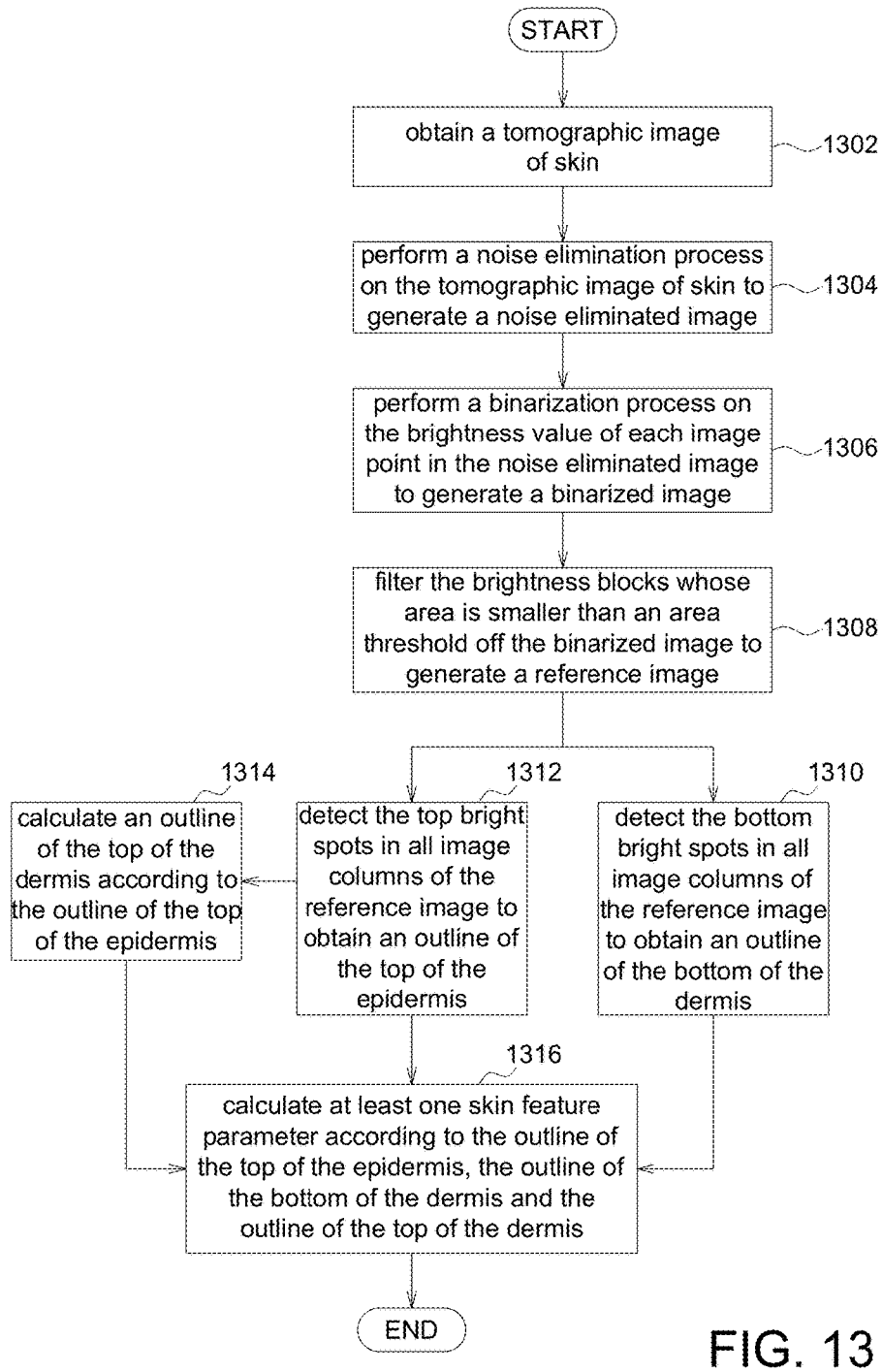
FIG. 13 is a flowchart of a method for evaluating skin tissue according to an embodiment of the disclosure.

FIG. 13 is a flowchart of a method for evaluating skin tissue according to an embodiment of the disclosure. The method for evaluating skin tissue can be performed by the image processor 106 of the skin tissue estimating system 100.

In step 1302, a tomographic image of skin I' is obtained by the image processor 106. As indicated in FIG. 14, the tomographic image of skin I' is captured from the image part of a target range of a tomographic gray level image of skin.

In step 1304, a noise elimination process is performed on the tomographic image of skin I' by the image processor 106 to generate a noise eliminated image FI.

In an embodiment, the noise elimination process includes: detecting an epidermal reflective area AA' from the tomographic image of skin I' by the image processor 106; setting the image points above the epidermal reflective area AA' and in the tomographic image of skin I' as dark spots to generate a pre-processed image PI; performing a spatial filtering process on the pre-processed image PI to generate a noise eliminated image FI. Wherein, the brightness values of the image points in the epidermal reflective area AA' are larger than a brightness threshold (such as the brightness value 245).

Figure 14:
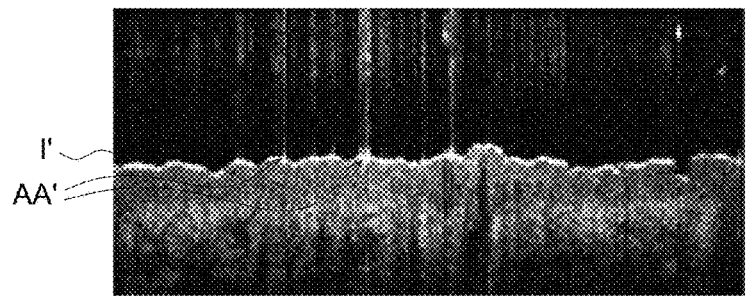
FIG. 14 is an exemplary tomographic image of skin.
Figure 15:
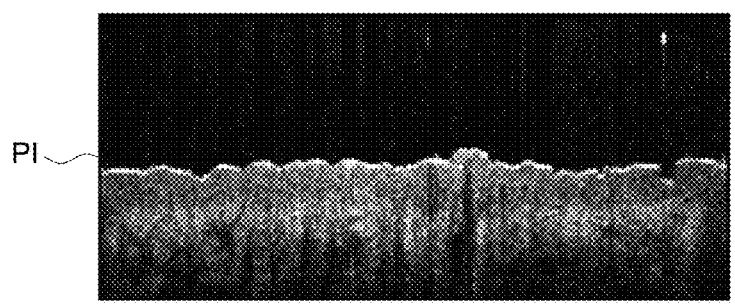
FIG. 15 is an exemplary pre-processed image.
Figure 16:
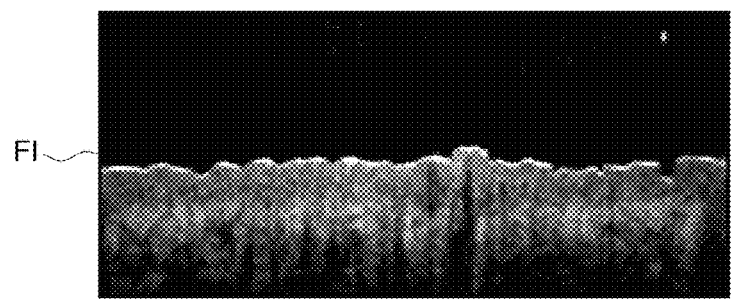
FIG. 16 is an exemplary noise eliminated image.

Refer to FIGS. 14~16. The image processor 106 locates the first image point whose brightness value is larger than a brightness threshold from each image column of the tomographic image of skin I' in a top down manner (that is, in a height decreasing direction), and regards the first image point as the top image point of the epidermal reflective area AA'. Since the part above the epidermal reflective area AA' (such as the air) is not the image of the skin tissue, the image processor 106 sets the image points above the top image point of the epidermal reflective area AA' in each image column as dark spots to filter off the linear streaks caused by the reflection of the light on the interface of the epidermis. Referring to FIG. 15, an exemplary pre-processed image PI generated according to the above mechanism is shown.

Since it is possible that some image columns do not have any image points whose brightness value is larger than the brightness threshold (that is, the top image point of the epidermal reflective area AA'), some noises or streaks still may exist in the pre-processed image PI. Therefore, the image processor 106 may further perform a spatial filtering process (such as a medium filter) on the pre-processed image PI to filter the independent noises or streaks not belonging to the skin tissue off the pre-processed image PI. As indicated in FIG. 16, an exemplary noise eliminated image FI generated by performing medium filtering process on the pre-processed image PI is shown.

Figure 17:
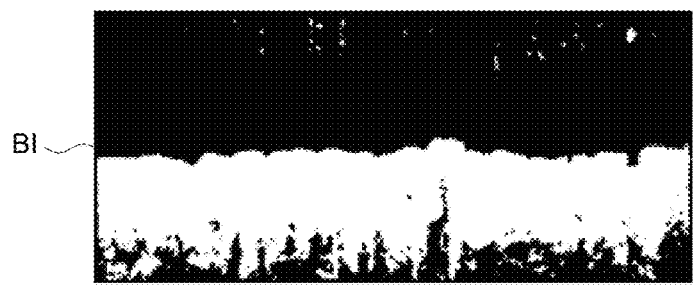
FIG. 17 is an exemplary binarized image.

In step 1306, a binarization process is performed on the brightness value of each image point in the noise eliminated image FI by the image processor 106 to generate a binarized image BI. For example, the image processor 106 sets the image points whose brightness value is not 0 as bright spots in the noise eliminated image FI, and sets the remaining image points as dark spots to generate a binarized image BI. As indicated in FIG. 17, the binarized image BI includes a plurality of bright blocks formed of aggregated bright spots.

In step 1308, the brightness blocks whose area is smaller than an area threshold is filtered off the binarized image BI by the image processor 106 to generate a reference image RI.

Figure 18:
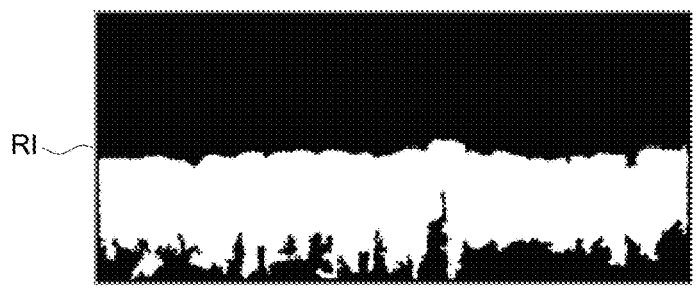
FIG. 18 is an exemplary reference image.

The area threshold can be determined according to the minimum area that the skin tissue structure may have in the binarized image BI. Let the area threshold=100 image points. Since the brightness blocks whose area is smaller than 100 image points possibly do not belong to the skin tissue structure, the brightness blocks whose area is smaller than 100 image points are set as dark spots and only the brightness blocks whose area is larger than 100 image points are preserved, such that the noises or streaks still existing in the binarized image BI can be filtered off. Referring to FIG. 18, an exemplary reference image RI generated by filtering some brightness blocks off the binarized image BI if the area threshold is 100 image points is shown.

As indicated in FIG. 18, the bright blocks in the reference image RI substantially covers the top of the epidermis to the bottom of the dermis. In other words, the top boundary and the bottom boundary of the bright blocks in the reference image RI correspond to the outline of the top of the epidermis and the outline of the bottom of the dermis, respectively. Furthermore, since the epidermis and the dermis have light and shade feature in the tomographic image of skin, and the outline of the top of the dermis is almost parallel to the outline of the top of the epidermis, the outline of the top of the dermis can be calculated from the outline of the top of the epidermis.

Details of the method are further described below with accompany drawings and steps 1310, 1312, 1314 and 1316.

Figure 19:
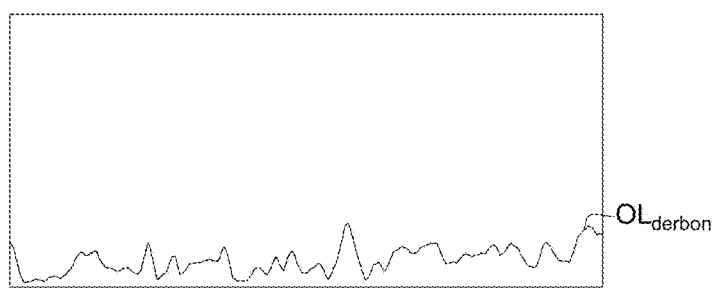
FIG. 19 is an exemplary outline of the bottom of the dermis detected in a reference image.

In step 1310, the bottom bright spots in all image columns of the reference image RI are detected by the image processor 106 to obtain an outline of the bottom of the dermis, wherein each of the bottom bright spots, unlike other bright spots in the corresponding image column, has a minimum height in a corresponding image column in the reference image RI. As indicated in FIG. 19, an exemplary outline of the bottom of the dermis $OL_{derbon}$ is detected from the reference image RI.

In an embodiment, a smoothing process is performed on the outline of the bottom of the dermis by the image processor 106 (for example, every N image columns are averaged) to obtain a more smoothed outline of the bottom of the dermis $OL_{derbon}$.

Figure 20:
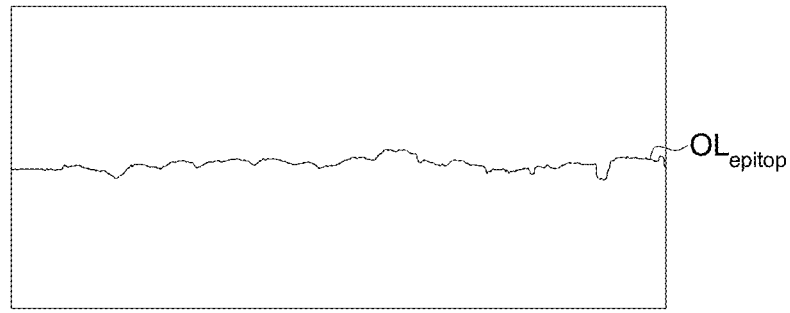
FIG. 20 is an exemplary outline of the top of the epidermis detected in a reference image.

In step 1312, the top bright spots in all image columns in the reference image RI are detected by the image processor 106 to obtain an outline of the top of the epidermis, wherein each of the top bright spots, unlike other bright spots in the corresponding image column, has a maximum height in a corresponding image column in the reference image RI. As indicated in FIG. 20, an exemplary outline of the top of the epidermis $OL_{epitope}$ is detected from the reference image RI.

In an embodiment, a smoothing process is performed on the outline of the top of the epidermis by the image processor 106 (for example, every N image columns are averaged) to obtain a more smoothed outline of the top of the epidermis $OL_{epitope}$.

In step 1314, the outline of the top of the dermis is calculated by the image processor 106 according to the outline of the top of the epidermis.

Figure 21:
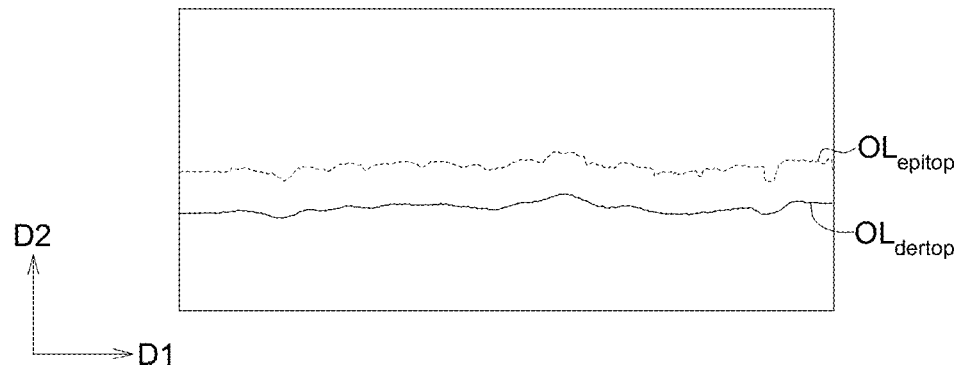
FIG. 21 is an exemplary outline of the top of the dermis obtained by shifting an outline of the top of the epidermis.

For example, the outline of the top of the epidermis can be sequentially shifted in a height decreasing direction from the position of the outline of the top of the epidermis (that is, the inverse direction of the second direction D2) in the tomographic image of skin I' or the noise eliminated image FI (or other non-binarized images such as the pre-processed image PI) by the image processor 106 to obtain a plurality of shifted outlines, and one of the shifted outlines is selected and used as the outline of the top of the dermis according to the average brightness value of each shifted outline, wherein, a largest variation in average brightness values exists between the outline of the top of the dermis and previous shifted outline. As indicated in FIG. 21, an exemplary outline of the top of the dermis $OL_{dertop}$ is obtained by shifting the outline of the top of the epidermis $OL_{epitop}$.

In an embodiment, the image processor 106 may detect a maximum tangent slope point from the histogram of the height of each shifted outline vs average brightness value and further selects one of the shifted outlines corresponding to the maximum tangent slope point as the outline of the top of the dermis $OL_{dertop}$.

In an embodiment, the image processor 106 performs a smoothing process on the obtained outline of the top of the dermis (for example, every N image columns are averaged) to obtain a more smoothed outline of the top of the dermis. As indicated in FIG. 21, the image processor 106 performs the smoothing process to obtain the outline of the top of the dermis $OL_{dertop}$ more smoothed than the outline of the top of the epidermis $OL_{epitop}$.

Details of obtaining the outline of the top of the dermis by shifting the outline of the top of the epidermis are illustratively described below with the non-limiting embodiment of FIG. 22.

Figure 22:
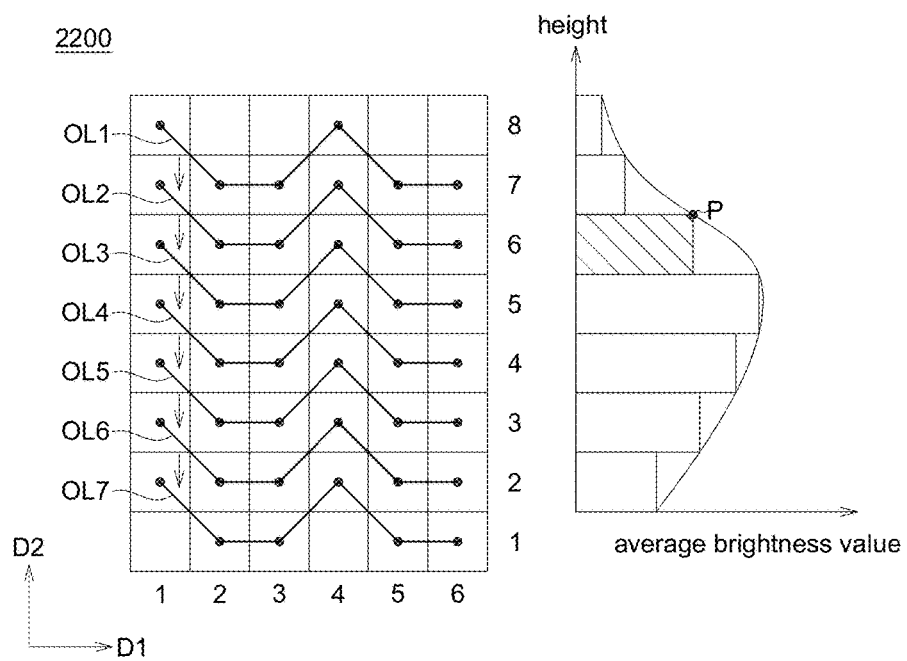
FIG. 22 is a schematic diagram of a partial image of a tomographic image of skin.

FIG. 22 is a schematic diagram of a partial image 2200 of a tomographic image of skin I'. The partial image 2200 includes many image points, and each image point is represented by a grid. Since the tomographic image of skin I' is a non-binarized image, the brightness value of each image point falls within a continuous range such as 0~255.

Curve OL1 shows an outline of the top of the epidermis in the tomographic image of skin I'. That is, the image points forming the curve OL1 have the same positions with the image points forming the outline of the top of the epidermis in the reference image RI.

Curves OL2~OL7 can be obtained by sequentially shifting curve OL1 in a height decreasing direction (that is, the inverse direction of the second direction D2).

The histogram of the heights of the curves OL1~OL7 vs average brightness value is at the right half of FIG. 22. Wherein, the heights of the curves OL1~OL7 are defined according to a selected image column. Let FIG. 22 be taken for example. The height of each of the curves OL1~OL7 is determined according to the height of the image point in the $1^{st}$ image column of the curve. Therefore, the heights of the curves OL1, OL2, OL3, OL4, OL5, OL6, and OL7 respectively are 8, 7, 6, 5, 4, 3, and 2. On the other hand, the average brightness value of a curve denotes the average value of the brightness values of all image points in the curve. Let the curve OL1 be taken for example. The average brightness value of curve OL1 denotes the average value of the brightness values of all image points whose coordinates are (1,8), (2,7), (3,7), (4,8), (5,7), and (6,7).

In the example of FIG. 22, the maximum tangent slope point of the histogram occurs at point P corresponding to the curve OL3 whose height is 6. This indicates that the curve OL3 is located at the light and shade junction of the partial image 2200. In the tomographic image of skin I', the dermal tissue has higher brightness than the epidermal tissue. Therefore, when the average brightness value of a curve is significantly larger than that of a previous curve (that is, has a largest variation in average brightness value), the curve will be regarded as a boundary between the dermis and the epidermis, that is, the outline of the top of the dermis. Thus, in the present example, the image processor 106 will use the curve OL3 as the outline of the top of the dermis.

Return to FIG. 13. In step 1316, at least one skin feature parameter is calculated by the image processor 106 according to the outline of the top of the epidermis, the outline of the bottom of the dermis and the outline of the top of the dermis.

Examples of skin feature parameters include at least one of epidermal thickness, dermal thickness, ratio of collagen distribution area, and collagen content index.

In an embodiment, the image processor 106 may calculate a height difference between the outline of the top of the epidermis and the outline of the top of the dermis in each image column, and further averages the height differences to obtain an epidermal thickness.

In an embodiment, the image processor 106 may calculate a height difference between the outline of the top of the dermis and the outline of the bottom of the dermis in each image column, and further averages the height differences to obtain a dermal thickness.

In an embodiment, the image processor 106 may create a dermal area from the tomographic image of skin I' or the noise eliminated image FI according to the outline of the top of the dermis and the outline of the bottom of the dermis, and further detect a plurality of target image points whose brightness values are larger than a brightness threshold from the dermal area, and calculate a ratio of the area of target image points to the dermal area to obtain a ratio of collagen distribution area.

In an alternate embodiment, the image processor 106 may further calculate an average brightness value of the target image points to obtain a collagen index positively correlated with the density of the dermal collagen.

Figure 23:
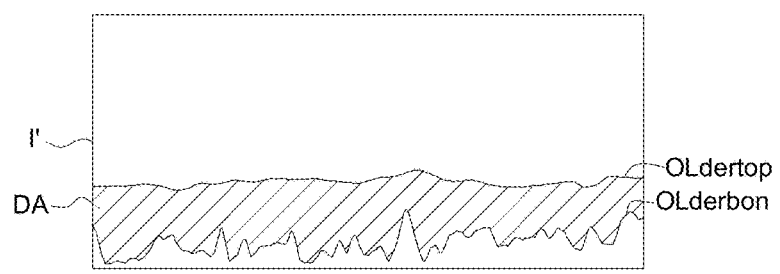
FIG. 23 is an exemplary dermal area constructed according to an outline of the top of the dermis and an outline of the bottom of the dermis.

As indicated in FIG. 23, after obtaining the outline of the top of the dermis $OL_{dertop}$ and the outline of the bottom of the dermis $OL_{derbon}$, the image processor 106 may regard the area between the two outlines $OL_{dertop}$ and $OL_{derbon}$ as a dermal area DA (presented by a slash area). Since the collagen content of the dermal tissue is positively correlated with the brightness value in the tomographic image of skin I', the image processor 106 may locate the area of the dermal tissue containing high collagen by detecting the image points (target image points) whose brightness values are larger than a brightness threshold, and further calculate the ratio of collagen distribution area in the dermal area DA. The image processor 106 can also calculate the average brightness value of the target image points to evaluate the richness of collagen in the dermal tissue. Generally speaking, the larger the average brightness value of the target image points, the higher the richness of collagen.

Figure 24:
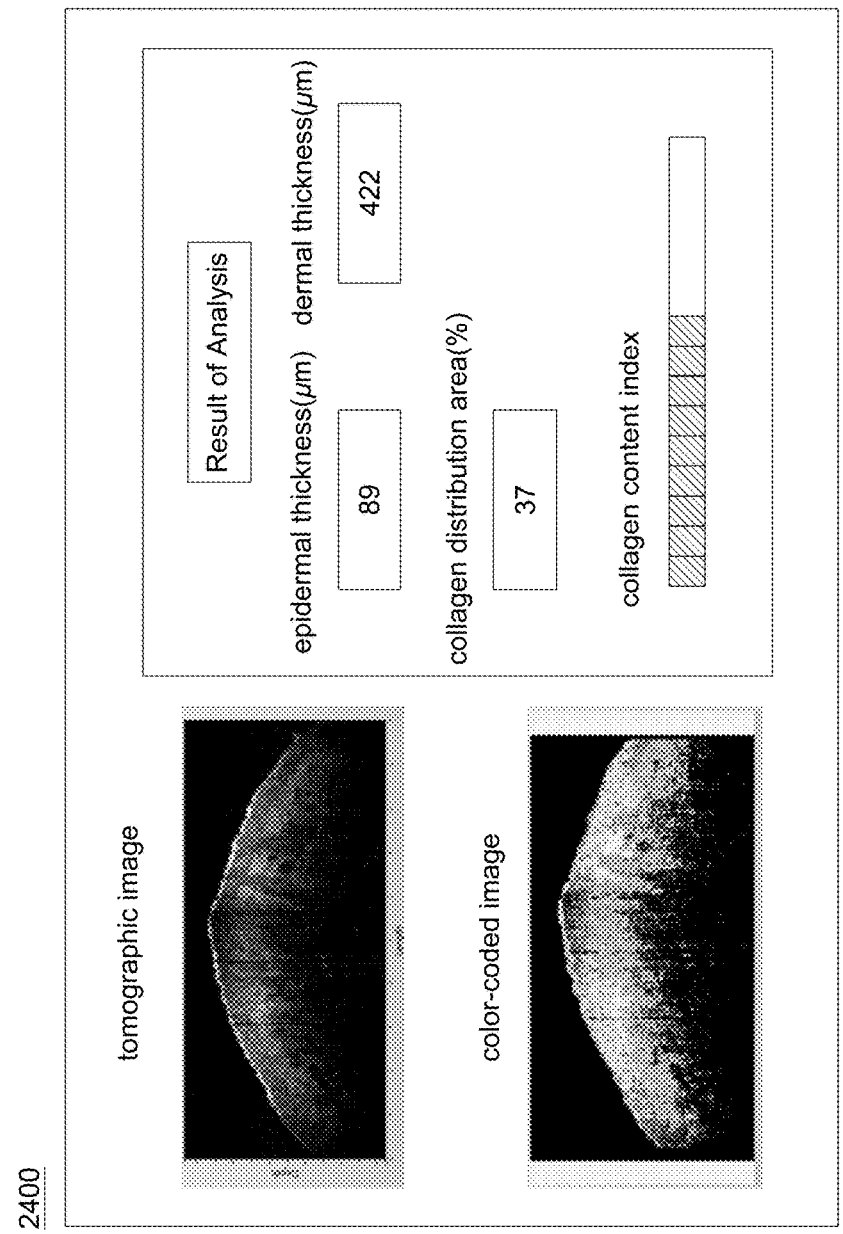
FIG. 24 is an exemplary patterned user interface.

FIG. 24 is an exemplary patterned user interface 2400. The patterned user interface 2400 shows one or more than one skin estimation parameter generated according to the method for evaluating skin tissue an embodiment of the disclosure. The patterned user interface 2400 can be displayed on the display monitor of the display device 108.

As indicated in FIG. 24, the patterned user interface 2400 can display estimated skin feature parameters, such as epidermal thickness, dermal thickness, collagen distribution area, and collagen content index, in "Result of Analysis" column.

In an embodiment, the patterned user interface 2400 can mark the epidermal area and the dermal area in the tomographic image of skin according to the outline of the top of the dermis, the outline of the bottom of the dermis and the outline of the top of the epidermis, and allocate different colors to different areas to help the user understand the distribution of the skin tissue.

To summarize, the disclosure provides a method for evaluating skin tissue and a system using the same capable of estimating relevant parameters of the testee's skin tissue according to the results of image processing of the tomographic image of skin.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for evaluating skin tissue, comprising:
obtaining a tomographic image of skin;
performing a quantization process for quantizing brightness values of the tomographic image of skin into a plurality of brightness levels to generate a quantized image;
performing a binarization process on the brightness value of each image point in the quantized image according to a first brightness threshold interval to generate a first filtered image, wherein in the quantized image, image points whose brightness values fall within the first brightness threshold interval are set as bright spots in the first filtered image, and image points whose brightness values fall outside the first brightness threshold interval are set as dark spots in the first filtered image;
performing the binarization process on the brightness value of each image point in the quantized image according to a second brightness threshold interval to generate a second filtered image, wherein in the quantized image, image points whose brightness values fall within the second brightness threshold interval are set as bright spots in the second filtered image, and image points whose brightness values fall outside the second brightness threshold interval are set as dark spots in the second filtered image;
obtaining a first estimated tissue boundary according to the distribution of the bright spots in the first filtered image;
obtaining a second estimated tissue boundary according to the distribution of the bright spots in the second filtered image; and
estimating a thickness of skin tissue according to a difference between the first and second estimated tissue boundaries.

2. The method for evaluating skin tissue according to claim 1, wherein the step of obtaining the first estimated tissue boundary further comprises:
performing a dilation and erosion process on the first filtered image to generate a repaired image, wherein the repaired image comprises a plurality of bright blocks formed of aggregated bright spots; and
calculating an estimated top position of dermis as the first estimated tissue boundary according to an average height of the bright blocks at a top of the repaired image.

3. The method for evaluating skin tissue according to claim 1, wherein the step of obtaining the second estimated tissue boundary further comprises:
detecting heights of a plurality of bottom bright spots of the second filtered image, wherein each of the bottom bright spots in a corresponding image column of the second filtered image, unlike other bright spots in the corresponding image column, has a minimum height; and
calculating the second estimated tissue boundary according to the heights of the plurality of bottom bright spots.

4. The method for evaluating skin tissue according to claim 3, further comprising:
determining whether the height of a first bottom bright spot of the plurality of bottom bright spots is larger than the first estimated tissue boundary; and
adjusting the height of the first bottom bright spot to be smaller than the first estimated tissue boundary if it is determined that the height of the first bottom bright spot is larger than the first estimated tissue boundary.

5. The method for evaluating skin tissue according to claim 3, further comprising:
determining whether a height difference between a first bottom bright spot of the plurality of bottom bright spots and a second bottom bright spot of the plurality of bottom bright spots is larger than a height threshold, wherein the first bottom bright spot and the second bottom bright spot are respectively located at two adjacent image columns in the second filtered image; and
determining whether a quantity of bright spots in a default segment above the first bottom bright spot in the image column is larger than a quantity threshold if it is determined that the height difference between the second bottom bright spot and the first bottom bright spot is larger than the height threshold; and
adjusting the height of the first bottom bright spot to the height of the second bottom bright spots if it is determined that the quantity of bright spots in the default segment is smaller than the quantity threshold.

6. The method for evaluating skin tissue according to claim 3, further comprising:
generating the second estimated tissue boundary according to a weighting average of an average height, a maximum height and a minimum height of the bottom bright spots.

7. The method for evaluating skin tissue according to claim 1, further comprising:
performing the binarization process on the brightness value of each image point in the quantized image according to a third brightness threshold interval to generate a third filtered image, wherein in the quantized image, the image points whose brightness values fall within the third brightness threshold interval are set as bright spots in the third filtered image, and the image points whose brightness values fall outside the third brightness threshold interval are set as dark spots in the third filtered image;
obtaining a third estimated tissue boundary according to the distribution of the bright spots in the third filtered image; and
estimating another thickness of skin tissue according to a difference between the third estimated tissue boundary and the first estimated tissue boundary.

8. The method for evaluating skin tissue according to claim 7, wherein the step of obtaining the third estimated tissue boundary further comprises:
detecting heights of a plurality of top bright spots in the third filtered image, wherein each of the top bright spots in a corresponding image column of the third filtered image, unlike other bright spots in the corresponding image column, has a maximum height; and
calculating the third estimated tissue boundary according to the heights of the top bright spots.

9. The method for evaluating skin tissue according to claim 8, further comprising:
determining whether a height difference between a first top bright spot of the plurality of top bright spots and a second top bright spot of the plurality of top bright spots is larger than a height threshold, wherein the first top bright spot and the second top bright spot are respectively located at two adjacent image columns in the third filtered image; and
adjusting the height of the first top bright spot such that the height difference between the first top bright spot and the second top bright spot is smaller than the height threshold if it is determined that the height difference between the first top bright spot and the second top bright spot is larger than the height threshold.

10. The method for evaluating skin tissue according to claim 9, wherein the step of adjusting the height of the first top bright spot further comprises:
   determining whether there are any bright spots existing within a default interval under the image column at which the first top bright spot is located;
   updating the first top bright spot as the bright spot having a maximum height in the default interval if it is determined that there are bright spots existing within the default interval; and
   adjusting the height of the first top bright spot to the height of the second top bright spot if it is determined that there are no bright spots existing within the default interval.

11. The method for evaluating skin tissue according to claim 8, further comprising:
   generating the third estimated tissue boundary according to a weighting average of an average height, a maximum height and a minimum height of the top bright spots.

12. The method for evaluating skin tissue according to claim 1, further comprising:
   obtaining an input image from an image capturing device; and
   performing an intensity normalization process on the input image, and using the intensity normalized input image as the tomographic image of skin,
   wherein the intensity normalization process comprises:
      detecting an average brightness value of a part of the input image corresponding to an epidermal reflective area; and
      shifting the overall brightness value of the input image until the average brightness value is adjusted to a default value.

13. A method for evaluating skin tissue, comprising:
   obtaining a tomographic image of skin;
   performing a noise elimination process on the tomographic image of skin to generate a noise eliminated image;
   performing a binarization process on the brightness value of each image point in the noise eliminated image to generate a binarized image, wherein the binarized image comprises a plurality of bright blocks formed of aggregated bright spots;
   filtering the plurality of brightness blocks whose area is smaller than an area threshold off the binarized image to generate a reference image;
   detecting bottom bright spots in all image columns of the reference image to obtain an outline of a bottom of a dermis, wherein each of the bottom bright spots in a corresponding image column of the reference image, unlike other bright spots in the corresponding image column, has a minimum height;
   detecting top bright spots in all image columns of the reference image to obtain an outline of a top of an epidermis, wherein each of the top bright spots in a corresponding image column of the reference image, unlike other top bright spots in the corresponding image column, has a maximum height;
   calculating an outline of a top of the dermis according to the outline of the top of the epidermis; and
   calculating at least one skin feature parameter according to the outline of the top of the epidermis, the outline of the bottom of the dermis and the outline of the top of the dermis.

14. The method for evaluating skin tissue according to claim 13, wherein the step of calculating the outline of the top of the dermis according to the outline of the top of the epidermis further comprises:
   sequentially shifting the outline of the top of the epidermis in a height decreasing direction from a position of the outline of the top of the epidermis in the tomographic image of skin or the noise eliminated image to obtain a plurality of shifted outlines;
   selecting one of the shifted outlines as the outline of the top of the dermis according to an average brightness value of each of the shifted outlines, wherein there is a largest variation in average brightness values existing between the outline of the top of the dermis and previous shifted outline.

15. The method for evaluating skin tissue according to claim 14, wherein the step of selecting one of the shifted outlines as the outline of the top of the dermis further comprises:
   creating a histogram of a height of each of the shifted outlines vs the average brightness value;
   detecting a maximum tangent slope point from the histogram; and
   selecting one of the shifted outlines corresponding to the maximum tangent slope point as the outline of the top of the dermis.

16. The method for evaluating skin tissue according to claim 13, wherein the noise elimination process comprises:
   detecting an epidermal reflective area from the tomographic image of skin, wherein the brightness value of each image point in the epidermal reflective area is larger than a brightness threshold;
   setting the image points above the epidermal reflective area as dark spots in the tomographic image of skin to generate a pre-processed image; and
   performing a spatial filtering process on the pre-processed image to generate a noise eliminated image.

17. The method for evaluating skin tissue according to claim 13, wherein the at least one skin feature parameter comprises an epidermal thickness, and the skin tissue analysis method further comprises:
   calculating a difference between a height of the outline of the top of the epidermis and a height of the outline of the top of the dermis in each image column; and
   averaging the differences to obtain the epidermal thickness.

18. The method for evaluating skin tissue according to claim 13, wherein the at least one skin feature parameter comprises a dermal thickness, and the skin tissue analysis method further comprises:
   calculating a difference between a height of the outline of the top of the dermis and a height of the outline of the bottom of the dermis in each image column; and
   averaging the differences to obtain the dermal thickness.

19. The method for evaluating skin tissue according to claim 13, wherein the at least one skin feature parameter comprises a ratio of collagen distribution area, and the skin tissue analysis method further comprises:
   creating a dermal area from the tomographic image of skin or the noise eliminated image according to the outline of the top of the dermis and the outline of the bottom of the dermis;

detecting a plurality of target image points whose brightness values are larger than a brightness threshold from the dermal area;

calculating a ratio of the area of target image points to the dermal area to obtain the ratio of collagen distribution area.

20. The method for evaluating skin tissue according to claim 13, wherein the at least one skin feature parameter comprises a collagen content index, and the skin tissue analysis method further comprises:

creating a dermal area from the tomographic image of skin or the noise eliminated image according to the outline of the top of the dermis and the outline of the bottom of the dermis;

detecting a plurality of target image points whose brightness values are larger than a brightness threshold from the dermal area;

calculating an average brightness value of the target image points to obtain the collagen content index.

21. A skin tissue estimating system, comprising:

an image capturing device used for capturing an input image;

a memory used for storing the programming code; and an image processor used for coupling the image capturing device and the memory and installed for:

obtaining the input image from the image capturing device;

performing an intensity normalization process on the input image to generate a tomographic image of skin;

performing a quantization process for quantizing brightness values of the tomographic image of skin into a plurality of brightness levels to generate a quantized image;

performing a binarization process on the brightness value of each image point in the quantized image according to a first brightness threshold interval to generate a first filtered image, wherein in the quantized image, the image points whose brightness values fall within the first brightness threshold interval are set as bright spots in the first filtered image, and the image points whose brightness values fall outside the first brightness threshold interval are set as dark spots in the first filtered image;

performing the binarization process on the brightness value of each image point in the quantized image according to a second brightness threshold interval to generate a second filtered image, wherein in the quantized image, the image points whose brightness values fall within the second brightness threshold interval are set as bright spots in the second filtered image, and the image points whose brightness values fall outside the second brightness threshold interval are set as dark spots in the second filtered image;

obtaining a first estimated tissue boundary according to the distribution of the bright spots in the first filtered image;

obtaining a second estimated tissue boundary according to the distribution of the bright spots in the second filtered image; and estimating a thickness of skin tissue according to a difference between the first and second estimated tissue boundaries.

* * * * *